United States Patent [19]

Jaber

[11] Patent Number: 5,574,167

[45] Date of Patent: Nov. 12, 1996

[54] ALKANOIC AND BENZOIC ESTERS OF 1-(2-HYDROXYPROPYL)-2-METHYL-5-NITROMOIMIDAZOLE

[76] Inventor: Santiago A. B. Jaber, Cerro Del Vigilanto No. 165, Col., Romero De Terreros, Mexico

[21] Appl. No.: 370,672

[22] Filed: Jan. 10, 1995

[30] Foreign Application Priority Data

Jan. 10, 1994 [MX] Mexico ..................... 940354

[51] Int. Cl.⁶ ............ C07D 233/84; C07D 233/94; A61K 31/415
[52] U.S. Cl. ............ 548/327.1; 514/398; 548/328.1
[58] Field of Search .......... 548/327.1; 514/398

[56] References Cited

U.S. PATENT DOCUMENTS

| | | | |
|---|---|---|---|
| 3,634,446 | 1/1972 | Hoffer et al. | 548/327.1 |
| 3,952,007 | 4/1976 | Rufer et al. | 548/328.1 |
| 4,020,166 | 4/1977 | Nesvadba et al. | 548/328.1 X |
| 4,089,968 | 5/1978 | Klaui | 548/327.1 X |
| 4,267,349 | 5/1981 | Hagen et al. | 548/328.1 |

FOREIGN PATENT DOCUMENTS

| | | | |
|---|---|---|---|
| 0140395 | 5/1985 | European Pat. Off. | 548/328.1 |
| 1079271 | 8/1967 | United Kingdom | 548/327.1 |

*Primary Examiner*—Floyd D. Higel
*Attorney, Agent, or Firm*—Harrison & Egbert

[57] ABSTRACT

The present invention is a method for producing a composition, and the composition, which is savorless, antiamoebic and antiprotozoan. This method includes the steps of mixing ram and dry secnidazole benzoil and methanol. This mixture is heated to reflux. The mixture is then cooled and filtered so as to form a solid product. The solid product is then dryed so as to produce pure secnidazole benzoil.

4 Claims, No Drawings

ALKANOIC AND BENZOIC ESTERS OF 1-(2-HYDROXYPROPYL)-2-METHYL-5-NITROMOIMIDAZOLE

TECHNICAL FIELD

The following invention refers basically to a chemical product antiamoebic & antiprotozoan as well as to the procedure to obtain it, with the advantage that it is savourless; thus it can be consumed by the patient without being afflicted by savours that are generally very offensive to human taste.

BACKGROUND OF THE INVENTION

Throughout history, pathogen microorganisms like the protozoa & mostly the amoeba have lived together with mankind causing health problems. There have existed likewise several methods trying to protect the mankind from these germs, the majority of them being very expensive because of the machinery employed, also the patient that suffers from these germs must go to a medical laboratory or hospital so as to be treated, having thus to pay for medical services and in some cases elevated hospitalization expenses. This problem is worse in the rural areas due to the deficiencies and the lack of hygiene. A large portion of these areas suffers almost in its totality from problems of amoeba.

Several scientists throughout the world have worked to find out a product which is antiamoebic and antiprotozoan, which is also easy to take and effective. It is important to emphasize that great part of these products used to prevent or to treat amoeba have a disagreeable flavour and taste and that eventually this taste turns out to be so strong and uncomfortable, that in some cases it can cause nausea, vomitting and sickness. For this reason, it is an object of the present invention to provide an effective chemical preparation in the control and treatment of amoeba and protozoa, but most of all to obtain a savourless product that would not cause troubles of flavour to the patients or to those that are trying to prevent diseases caused by these micoorganisms.

DETAILED DESCRIPTION OF THE PRESENT INVENTION

The present invention is a chemical that can be used to provide the advantages recited hereinbefore.

The following formula is the result of the long research work that was achieved over a long period of time.

SECNIDAZOLE BENZOYL

FORMULA:
1-(2-hydroxypropyl)-2-methyl-5-nitroimidazole benzoate

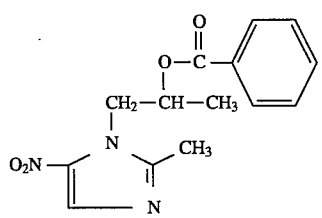

$C_{14}H_{16}N_3O_4$    Molecular Weight: 290.29

PROCEDURE DESCRIPTION

In a flask with a stirrer and a condenser load 200 g. of secnidazole, 900, c.c, of toluene and 195 c.c., of pyridine, heat up to 70°–80° C. and add slowly during 60 min. 192 c.c, of benzoyl chloride. When the addition is finished, the mixture is heated to reflux during two hours. Afterward, wash 3 times with 500 c.c. of water each time. The organic layer is cooled up to 0 C. during 15 min., and it is filtered. The filtered is washed with 50 c.c. of cold toluene and is dried, and thus are is obtained 200 g. of raw and dry secnidazole benzoyl.

PURIFICATION

In a flask provided with a stirrer and a condenser, load 200 g. of secnidazole benzoyl raw and dry, and 600 c.c. of methanol, heat to reflux during 30 min., and afterwards cool up to 0 C., keeping this temperature during one hour. It is then filtered and the solid product is dried; thus are obtained 190–195 gms. of pure secnidazole benzoyl.

The previous constitutes the procedure to obtain a pure chemical product savorless, antiamoebic and antiprotozoan.

With the same procedure and changing from the formula the acyl chloride or the corresponding anhydride, esters of aliphatic or aromatic acids are obtained, that correspond to the following general formula:

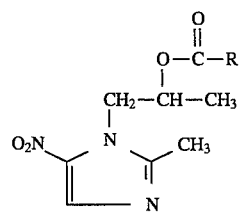

Where $R=-(CH_2)_n-CH_3$ and where n is a straight chain alkyl of 6 to 18 carbon atoms, that could be in an illustrative way, but not limiting: the caproate, enantate, palmitate, stearate, succinate, propionate and valerianate.

I claim:

1. A savorless, antiamoebic and anti-protozoan compound which has the formula:

1-(2-hydroxypropyl)-2-methyl-5-nitromidazole benzoate

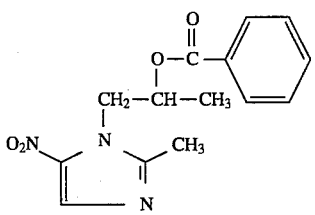

SECNIDAZOLE BENZOYL.

2. A savorless, antiamoebic and antiprotozoan water-insoluble compound having the formula:

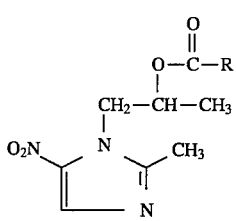

where $R = -(CH_2)_n - CH_3$ and where n is a number 5 to 17.

3. A procedure to obtain a savorless, antiamoebic and antiprotozoan chemical product, that comprises the steps of:

mixing in a flask 1-(2-hydroxypropyl)-2-methyl-5-nitromidazole benzoate, toluene, and pyridine;

heating the mixture to between 70°–80° C. while adding benzoyl chloride and heating again to reflux for 2 hours;

washing the heated mixture 3 times with of water;

cooling an organic layer of the washed heated mixture to 0° C. for 15 min.;

filtering the cooled organic layer so as to obtain a filtrate;

washing the filtrate with cold toluene; and drying the washed filtrate so as to obtain raw and dry 1-(2-hydroxypropyl)-2-methyl-5-nitromidazole benzoate.

4. A procedure to obtain a savorless, antiamoebic and antiprotozoan compound comprising the steps of:

mixing in a flask raw and dry and of methanol;

heating the mixture to reflux;

cooling the heated mixture to 0° C. for over one hour;

filtering the cooled mixture so as to form a solid product; and drying the solid product so as to obtain pure 1-(2-hydroxypropyl)-2-methyl-5-nitromidazole benzoate.

* * * * *